US010682361B2

(12) United States Patent
Whitcup et al.

(10) Patent No.: US 10,682,361 B2
(45) Date of Patent: Jun. 16, 2020

(54) SUSTAINED RELEASE BIMATOPROST, BIMATOPROST ANALOGS, PROSTAMIDES AND PROSTAGLANDINS FOR FAT REDUCTION

(71) Applicant: ALLERGAN, INC., Irvine, CA (US)

(72) Inventors: Scott Whitcup, Laguna Hills, CA (US); David Woodward, Lake Forest, CA (US); Patrick Hughes, Aliso Viejo, CA (US)

(73) Assignee: Allergan, Inc., Irvine, CA (US)

( * ) Notice: Subject to any disclaimer, the term of this patent is extended or adjusted under 35 U.S.C. 154(b) by 1 day.

(21) Appl. No.: 15/134,792

(22) Filed: Apr. 21, 2016

(65) Prior Publication Data

US 2016/0339039 A1    Nov. 24, 2016

Related U.S. Application Data

(63) Continuation of application No. 14/248,898, filed on Apr. 9, 2014, now abandoned.

(60) Provisional application No. 61/811,682, filed on Apr. 12, 2013.

(51) Int. Cl.
| | | |
|---|---|---|
| *A61K 9/00* | (2006.01) | |
| *A61K 31/5575* | (2006.01) | |
| *A61K 31/559* | (2006.01) | |
| *A61K 47/34* | (2017.01) | |
| *A61K 47/32* | (2006.01) | |
| *A61K 47/36* | (2006.01) | |
| *A61K 9/06* | (2006.01) | |
| *A61K 9/19* | (2006.01) | |
| *A61K 9/16* | (2006.01) | |
| *A61K 31/381* | (2006.01) | |
| *A61K 47/10* | (2017.01) | |
| *A61K 9/08* | (2006.01) | |

(52) U.S. Cl.
CPC ........ *A61K 31/5575* (2013.01); *A61K 9/0019* (2013.01); *A61K 9/0024* (2013.01); *A61K 9/0051* (2013.01); *A61K 9/06* (2013.01); *A61K 9/1647* (2013.01); *A61K 9/1652* (2013.01); *A61K 9/19* (2013.01); *A61K 31/381* (2013.01); *A61K 31/559* (2013.01); *A61K 47/10* (2013.01); *A61K 47/32* (2013.01); *A61K 47/34* (2013.01); *A61K 47/36* (2013.01); *A61K 9/08* (2013.01)

(58) Field of Classification Search
CPC .... A61K 31/557; A61K 31/5575; A61K 9/06; A61K 9/08; A61K 9/10; A61K 9/107; A61K 9/0019; A61K 8/04; A61K 8/042; A61K 8/044
See application file for complete search history.

(56) References Cited

U.S. PATENT DOCUMENTS

| | | | |
|---|---|---|---|
| 6,124,344 A | 9/2000 | Burk | |
| 7,666,912 B2 * | 2/2010 | Grosskreutz | ....... A61K 31/5575 514/622 |
| 9,795,615 B2 | 10/2017 | Poloso et al. | |
| 2010/0234466 A1 | 9/2010 | Grosskreutz et al. | |
| 2011/0111006 A1 | 5/2011 | Wong et al. | |

FOREIGN PATENT DOCUMENTS

| | | | | |
|---|---|---|---|---|
| EP | 2218424 A1 * | 8/2010 | ........... | A61F 9/0017 |
| JP | 59155313 | 9/1984 | | |
| JP | 11505802 | 5/1995 | | |
| JP | 2007515494 | 6/2007 | | |
| JP | 2009167197 | 7/2009 | | |
| JP | 2012521997 | 9/2012 | | |
| WO | WO-9636599 A1 * | 11/1996 | ........... | A61K 31/557 |
| WO | 2004037268 | 5/2004 | | |
| WO | WO2004037268 A1 | 5/2004 | | |
| WO | 2007-111806 | 10/2007 | | |
| WO | WO-2007111806 A2 * | 10/2007 | ......... | A61K 31/5575 |
| WO | 2008-070402 | 6/2008 | | |
| WO | 2008067060 | 12/2008 | | |
| WO | 2010056598 | 12/2010 | | |
| WO | 2011-109384 | 9/2011 | | |
| WO | 2012012546 | 1/2012 | | |
| WO | 2014143754 | 9/2014 | | |

OTHER PUBLICATIONS

Choi et al (In vitro Study of Antiadipogenic Profile of Latanoprost, Travoprost, Bimatoprost, and Tafluprost in Human Orbital Preadipocytes; Journal of Ocular Pharmacology and Therapeutics, vol. 28, No. 2, 2012, pp. 146-152) (Year: 2012).*
Choi, Hee Young et al, In Vitro Study of Antiadipogenic Profile of Latanoprost, Travoprost, Bimatoprost, and Tafluprost in Human Orbital Preadiopocytes, Journal of Ocular Pharmacology and Therapeutics, 2012, 146-152, 28(2).
International Search Report & Written Opinion dated Aug. 29, 2014 for PCT/US14/33558 filed Apr. 9, 2014 in the name of Allergan, Inc.
Gaikwad, P.L., et al., The Use of Bioisosterism in Drug Design and Moiecuiar Modification, Amer. J. Pharmatech Res., 2012, pp. 1-23, 2 (4).

* cited by examiner

*Primary Examiner* — Micah Paul Young
(74) *Attorney, Agent, or Firm* — Jonathan Bass (57) ABSTRACT

The present invention is directed to compositions and methods for injection into fat deposits for sustained release of compounds which result in localized fat reduction.

9 Claims, 10 Drawing Sheets

SUSTAINED RELEASE BIMATOPROST, BIMATOPROST ANALOGS, PROSTAMIDES AND PROSTAGLANDINS FOR FAT REDUCTION

CROSS REFERENCE TO RELATED APPLICATION

This application is a continuation of U.S. patent application Ser. No. 14/248,898, filed Apr. 9, 2014, which in turn claims the benefit of U.S. Provisional Patent Application Ser. No. 61/811,682, filed Apr. 12, 2013, the disclosures of which are hereby incorporated by reference in their entireties and serve as the basis of a priority and/or benefit claim for the present application.

SUMMARY OF THE INVENTION

The present invention is directed to compositions and methods for the sustained release of bimatoprost, bimatoprost analogs, bimatoprost prodrugs, prostamides, prostaglandins, prostaglandin analogs and prostaglandin derivatives from injectable and implantable depots for the purpose of fat reduction including localized fat reduction.

Topical bimatoprost has been shown to effectively prevent apidocyte formation and maturation and to atrophy adipocytes in animal models after topical administration. Furthermore, clinical evidence of fat reduction after topical administration of bimatoprost has been reported. The present invention is directed to sustained release methods and formulations of bimatoprost, bimatoprost analogs, bimatoprost prodrugs, prostamides, prostaglandins, prostaglandin analogs and derivatives and prostaglandin analogs such as latanoprost and travoprost for localized fat reduction.

Some embodiments of the invention are included in the following paragraphs:

1) A method of fat reduction comprising injecting a sustained release formulation of a compound selected from the group consisting of bimatoprost, bimatoprost analogs, bimatoprost prodrugs, prostamides, prostaglandins, prostaglandin analogs, latanoprost and travoprost and prostaglandin derivatives and mixtures thereof into a fat deposit.
2) The method of paragraph 1 wherein the compound is selected from the group consisting of bimatoprost, latanoprost, travoprost and Compound #1 and mixtures thereof.
3) The method of paragraph 1 wherein the sustained release formulation is selected from the group consisting of injectable depots, gel suspensions, a ReGel delivery system, a hyaluronic acid release platform, implants, microspheres, macrospheres and injectable solvents.
4) The method of paragraphs 2 or 3 wherein the compound is bimatoprost.
5) The method of paragraphs 1-4 wherein the sustained release formulation is injected directly into the fat deposit.
6) The method of paragraph 1 wherein the fat reduction is localized fat reduction at and around the injection site.
7) The method of paragraphs 1 or 3 wherein the sustained release formulation is an implant with the formulation of about 20% bimatoprost, about 45% R203s, about 20% RG752s, about 10% R202H and about 5% PEG-3350.
8) The method of paragraphs 1 or 3 wherein the method results in atrophy of both brown and white adipocytes and results in localized fat reduction.
9) The method of paragraph 7 wherein the implant releases bimatoprost in the fat deposit for over a period of 100 days.
10) The method of paragraph 1 wherein the sustained release formulation releases the compound systemically to target a fat deposit at a location in the body that is not at the location of the sustained released formulation or at difficult to reach areas.
11) The method of paragraphs 1 or 10 wherein the sustained release formulations are injected or implanted at a location that permits reduction of abdominal fat deposits, visceral fat deposits, epicardial fat deposits, subcutaneous fat deposits and ectopic fat deposits as non-limiting examples.
12) A composition for use in localized fat reduction wherein the composition is a sustained release composition selected from the group consisting of injectable depots, gel suspensions, a ReGel delivery system, a hyaluronic acid based platform, implants, microspheres, macrospheres and injectable solvents.
13) The composition of paragraph 12 wherein the composition further comprises a compound selected from the group consisting of bimatoprost, bimatoprost analogs, bimatoprost prodrugs, prostamides, prostaglandins, prostaglandin analogs, latanoprost and travoprost and prostaglandin derivatives.
14) The composition of paragraph 12 and 13 wherein the sustained release composition is a Regel delivery system and the compound is bimatoprost.
15) The composition of paragraph 14 wherein the composition is injected into a localized fat deposit.

16) The composition of paragraph 15 wherein the composition is injected at multiple injection sites into a single localized fat deposit.
17) The composition of paragraph 15 wherein the composition releases bimatoprost into the localized fat deposit for over a period of 100 days.
18) The composition of paragraph 12 or 13 wherein the sustained release formulation is an implant comprised of about 20% bimatoprost, about 45% R203s, about 20% RG752s, about 10% R202H and about 5% PEG-3350.
19) The composition of paragraph 18 wherein the composition is injected into at least one selected from the group consisting of abdominal fat deposits, visceral fat deposits, epicardial fat deposits, subcutaneous fat deposits and ectopic fat deposits.
20) The composition of paragraph 18 wherein injection of the composition results in atrophy of adipocytes in the localized fat deposit and reduction of localized fat.
21) The composition of paragraph 12 or 13 wherein the sustained release formulation is an implant comprised of at least one polymer selected from the group consisting of poly(d,l-lactide-co-glycolide), poly (d,l-lactide), poly(caprolactone), poly(dioxanone), poly(ethylene glycol), poly(ortho-ester), polyesters, poly(phosphazine), poly (phosphate ester), polycaprolactone, silicone, natural polymers such as latex, gelatin or collagen, or polymeric blends and the compound is selected from the group consisting of bimatoprost, latanoprost, travoprost and mixtures thereof.
22) The composition of paragraph 12 or 13 wherein the sustained release formulation is a gel suspension comprised of at least one compound selected from the group consisting of sodium hyaluronate, crosslinked hyaluronic acid, chondroitin sulfate, cellulosics, gelatin, collagen, glycosaminoclycans, or other synthetic or naturally occurring polysaccharides and the compound is selected from the group consisting bimatoprost, latanoprost, travoprost and mixtures thereof.
23) The composition of paragraph 22 wherein the gel suspension is a thermal gelling delivery system.
24) The composition of paragraph 22 wherein the thermal gelling system is comprised of solutions of A-B-A or B-A-B triblock copolymers or B-A block copolymers.
25) The composition of paragraph 12 or 13 wherein the sustained release formulation is an injectable depot with biocompatible solvents selected from the group consisting of DMSO, NMP and DMAC or mixtures thereof.

DETAILED DESCRIPTION OF THE INVENTION

Bimatoprost and other compounds can be dissolved or dispersed in a gel, in a biodegradable solid implant, or biocompatible solvents containing solvated polymers, which can form solid depots upon injection. Additionally, thermal gelling delivery systems of bimatoprost may also be utilized. Solid implants for sustained release may be comprised of poly(d,l-lactide-co-glycolide), poly (d,l-lactide), poly(caprolactone), poly(dioxanone), poly(ethylene glycol), poly(ortho-ester), polyesters, poly(phosphazine), poly(phosphate ester), polycaprolactone, silicone, natural polymers such as latex, gelatin or collagen, or polymeric blends. Gel suspensions could contain sodium hyaluronate, cross-linked hyaluronic acid, chondroitin sulfate, cellulosics, gelatin, collagen, glycosaminoclycans, or other synthetic or naturally occurring polysaccharides. Biocompatible solvents for injection of in situ forming depots include DMSO (dimethyl sulfoxide), NMP (N-methylpyrrolidone), DMAC (dimethylacetamide), or other non-aqueous solvents for injection.

Bimatoprost delivery systems and delivery systems for other compounds can be administered for reduction of adipose tissue through the injection or implantation of implants or injectable depots. Such delivery systems may be used for reduction of local adipose tissue, e.g subcutaneous fat, and/or as a method for sustained systemic delivery to achieve reduction of visceral fat and other fat pad depositions that are not easily reached by local administration of the implant or injection such as pericardial fat depositions. Bimatoprost is a low melting compound and the ability to sustain its release from multiple delivery platforms is surprising. Specific delivery platforms include but are not limited to injectable bimatoprost delivery depots, in situ forming bimatoprost depots, hyaluronic acid depots, solid form bimatoprost implants, bimatoprost microspheres and injectable solvent depots.

The delivery systems of the present invention can be injected or implanted at a location to achieve reduction of subcutaneous fat deposits and adipose tissue such as abdominal fat, visceral fat, epicardial fat, submental fat, periorbital fat and ectopic fat pads.

Example I

Injectable Depots

PLGA and multiblock polymers have been shown to release bimatoprost upon depot formation. The polymers and drug are dissolved in a biocompatible solvent for both, such as N-methypyrrolidinone, di-methyl acetamide or DMSO. The formulation is sterile filtered, autoclaved, or irradiated for sterility. The solution is filled into a sterile vial or a unit dose syringe. After injection, the biocompatible solvent diffuses away from the depot, leaving behind a firm prostamide or prostaglandin loaded implant. The depot releases bimatoprost, prostamide or prostaglandin for days, weeks, or months, as the polymer bioerodes. Drug loading in solution could range from 0.1% to 50%. Polymer loading in solution could range from 15% to 50%. Excipients could include poly(ethylene glycol), short chain fatty acids, waxes, cholesterol, aliphatic alcohols, co-solvents, or other compounds which would adjust the hydrophobicity of the depot.

Figure 1:
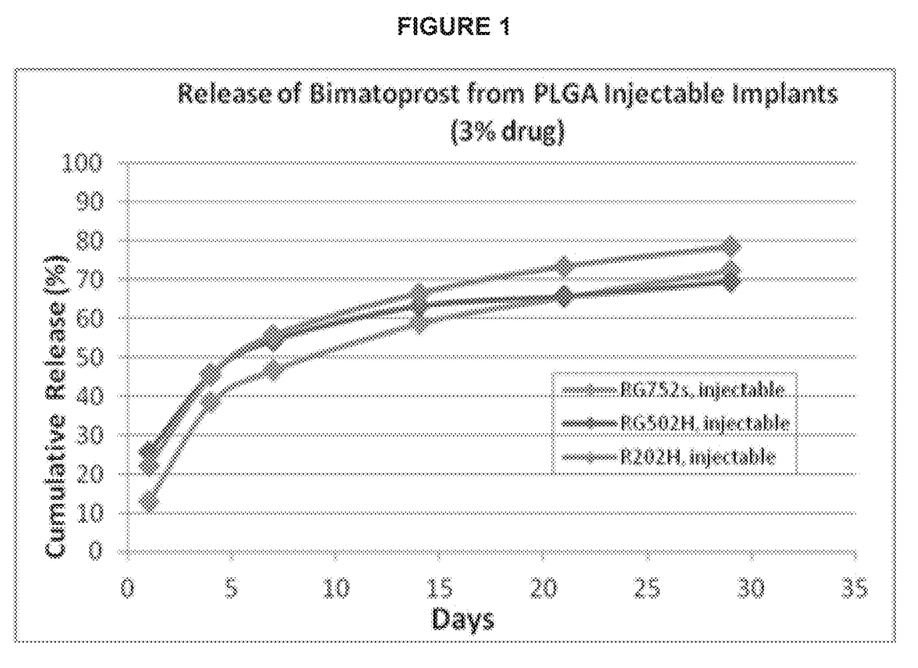
FIG. 1 shows in vitro release profiles of brimatoprost with injectable PLGA implants.
Figure 2:
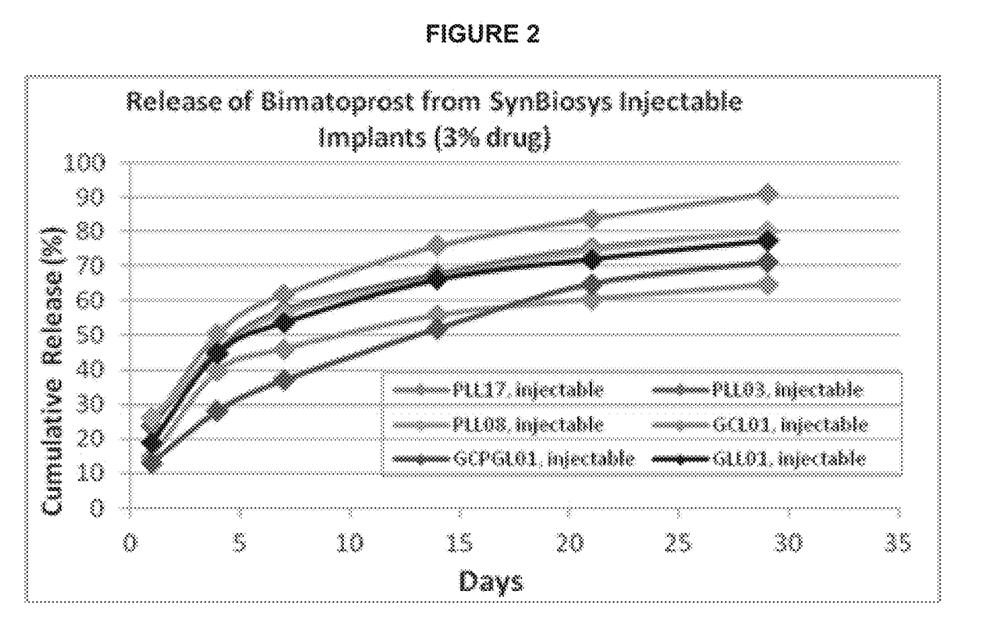
FIG. 2 shows in vitro release profiles of brimatoprost with injectable SynBiosys implants.

With both PLGA and SynBiosys bimatoprost containing injectable depots, the drug was continuously released for at least one month as shown in FIGS. 1 and 2. It is possible to further optimize the release kinetics by varying drug load, polymer concentration, polymer properties, formulation excipients or DMSO volume used for implant preparation.

Example II

ReGel Delivery System

Polymer systems that undergo phase transitions in response to various stimuli can also be used. This phase transition results in a significant volume and or viscosity change in the system. The system can respond to pH, ionic environment, temperature, biologic triggers as well as other chemical and physical triggers. The system comprises one or more polymers capable of interacting to cause a phase-transition resulting in the volume or viscosity increases. Examples of polymers include polyacrylic acid and polyethylene oxide copolymers. Other components of the system include excipients known to those experienced in the art.

The system has the further advantage of offering controlled and sustained release of therapeutically active agents to local tissues. The drug may be physically entrapped or chemically bound via covalent linkages, hydrogen binding, ionic interactions, van der Waals forces or hydrophobic interactions. Release of the drug can be controlled by physical entrapment of the active compound in the transitioned gel. Compounds can also be physically or chemically bound to the polymers comprising the phase transition gel. The phase transition of the gel serves to create a depot for drug delivery.

A specific example of this invention teaches the use of thermal gelling bimatoprost deliver delivery systems comprised of solutions of A-B-A or B-A-B triblock copolymers or B-A block copolymers where A=polylactide-co-glycolide (PLGA/PLA) and B=polyethylene oxide (PEO) and latanoprost. These polymers make up the Regel in situ gelling delivery system. Its aqueous solutions have shown to have sol-to-gel transition behavior as temperature increases. For drug delivery applications, gelation at physiologically relevant temperature (e.g., 37° C.) is particularly important and forms the basis for the utility of the systems for medical and drug delivery purposes.

Figure 3A:
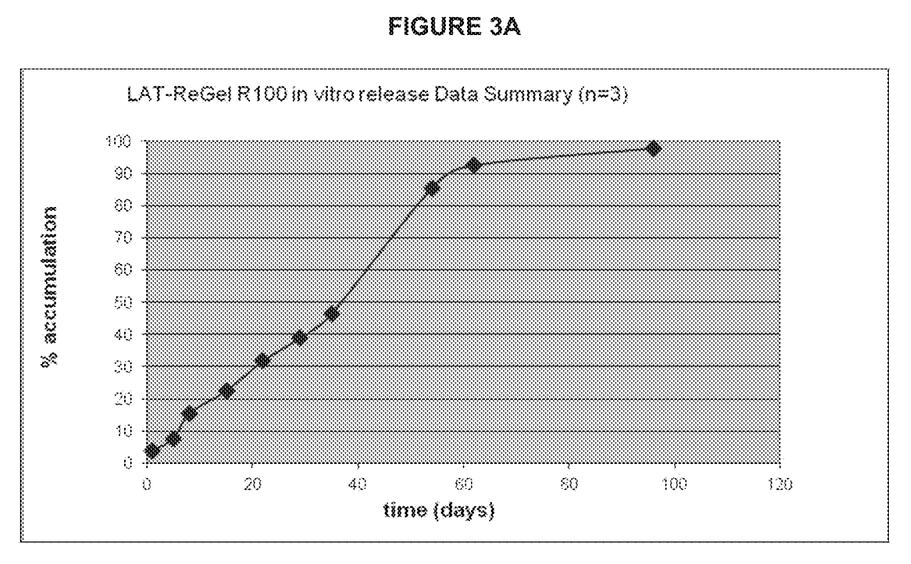
FIGS. 3A and 3B show 100 day ReGel 100 or ReGel B release data.
Figure 3B:
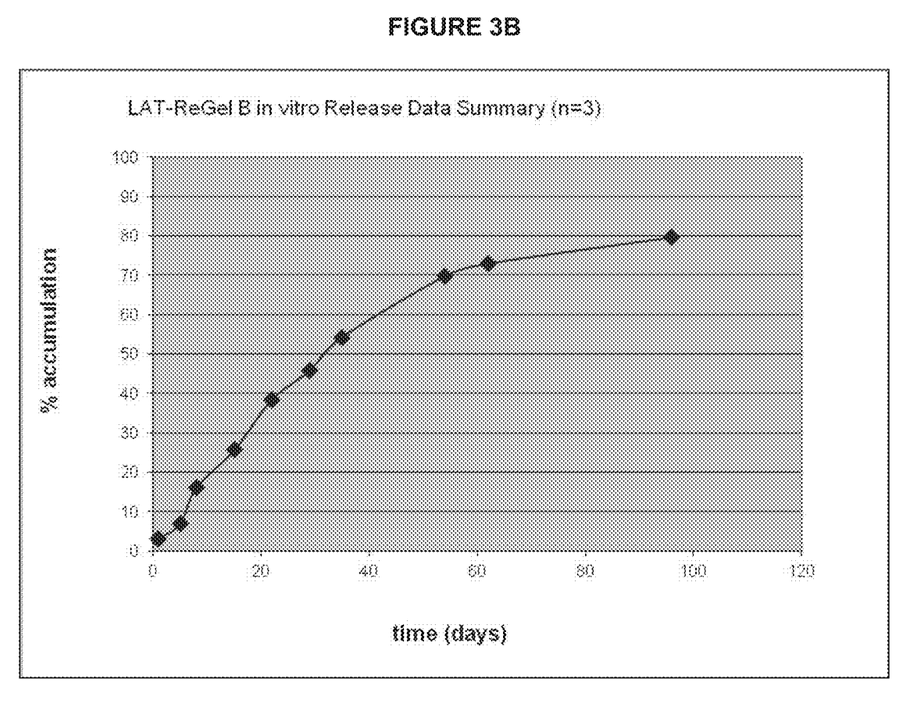
Figure 4A:
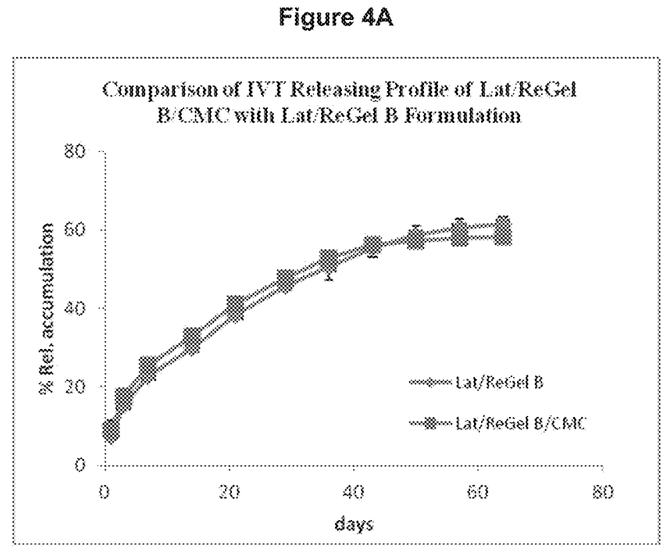
FIGS. 4A-4C show a comparison of latanoprost release data of ReGel 100 or ReGel B delivery systems.
Figure 4B:
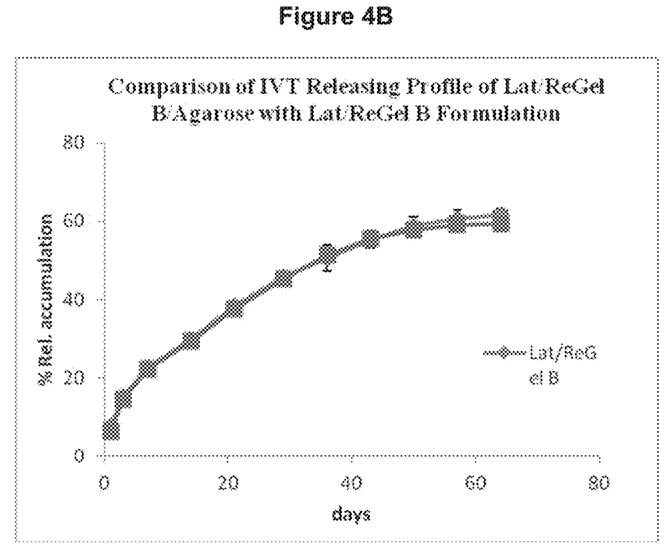
Figure 4C:
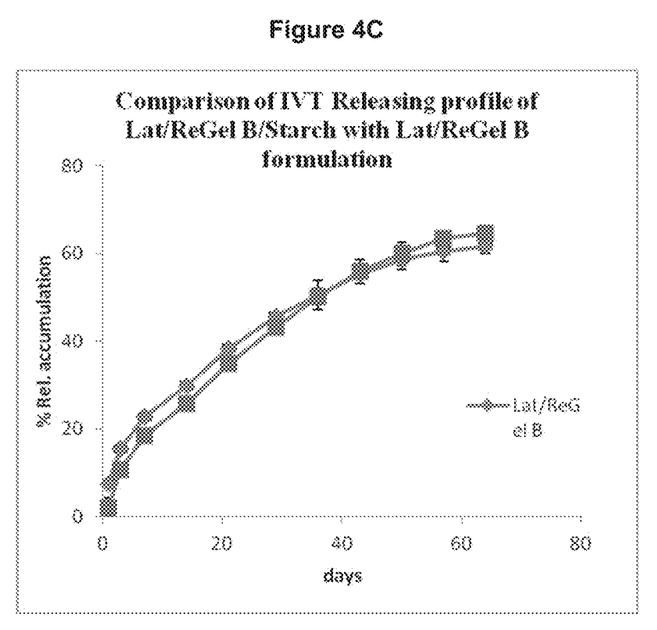

In the specific example, latanoprost was loaded at 3% loading into ReGel 100 or ReGel B i.e. 3 mg drug in 100 ul gel. The system displayed sustained release after thermal gelation with no burst of latanoprost. This is very surprising given the relative low melting point and solubility of latanoprost. i.e., slow release, no burst. The gel remained for longer than 100 days as shown in FIGS. 3A and 3B. Additional modifications can be made by adding other polymers to the system, e.g., CMC, agarose and starch.

Example III

Hyaluronic Acids

Crosslinked hyaluronic acid has been shown to localize upon injection providing a potential sustained release platform. Drug can either be incorporated into the crosslinked hyaluronic acid or conjugated to the vehicle for sustained release. In the case of the former, release and erosion of the platform can be controlled by porosity of the gel, length of the crosslinkers and crosslinking density. Alternatively, in the latter case, bimatoprost or a prostamide analog can be covalently or ionically bonded to the hyaluronic backbone through one of several linkers known to the art. Finally, drug may be incorporated into another sustained release modality, such as microspheres, then incorporated into the hyaluronic acid (crosslinked or non-crosslinked) and injected as a delivery platform.

Figure 5:
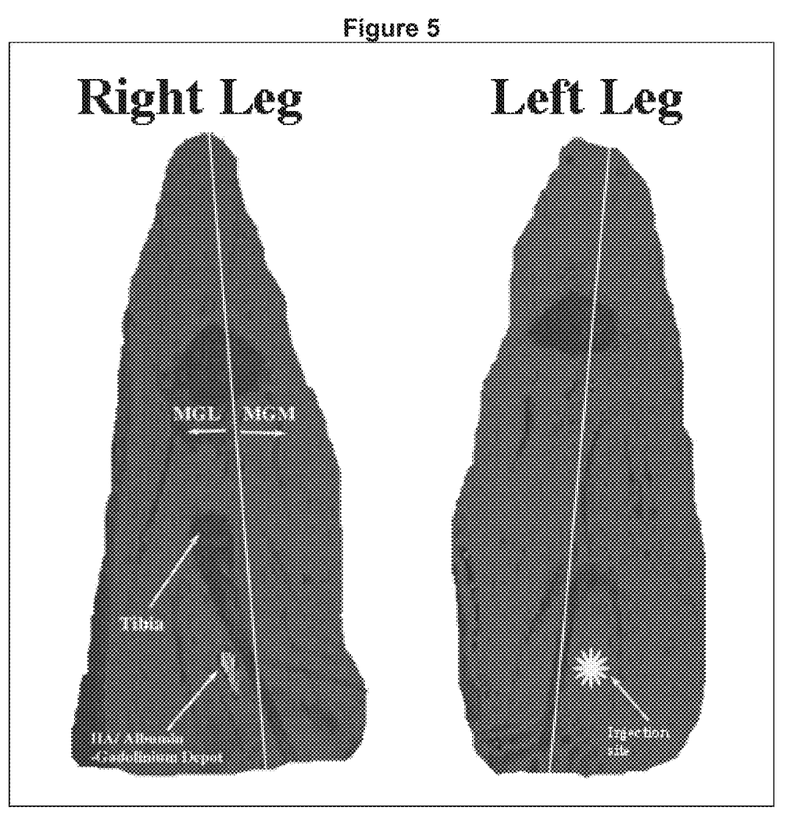
FIG. 5 shows a 2-D MR image 40 minutes post-injection oriented longitudinal through the gastrocnemius muscle to show the MGL and MGM muscle groups in each leg. The right leg was injected with HA/Albumin-Gadolinium, the left leg with Albumin-Gadolinium alone.

FIG. 5 shows a 2-D MR image 40 minutes post-injection oriented longitudinal through the gastrocnemius muscle to show the MGL (tripennate gastrocnemius lateralis) and MGM (unipennate gastrocnemius medialis) muscle groups in each leg. The right leg was injected with HA/Albumin-Gadolinium, the left leg with Albumin-Gadolinium alone. The left leg shows diffuse spread of the Albumin-Gadolinium (blue color) throughout the MGL muscle and crossover to the adjacent MGM muscle. This data shows that cross-linked HA depots can be localized and provide a platform for the local sustained release of a prostaglandin or prostamide for fat reduction.

Example IV

Implants

Figure 6:
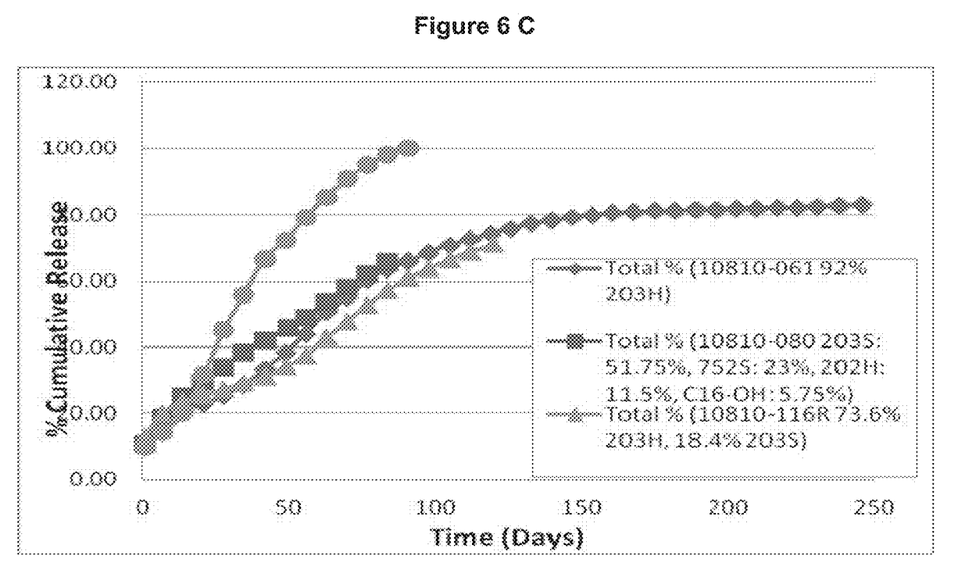
FIG. 6A shows the release rate of bimatoprost in a formulation of 20% Bimatoprost, 45% R203s, 20% RG752s 10% R202H, 5% PEG-3350.
FIG. 6B shows the release rate of bimatoprost in a formulation shown at the bottom of FIG. 6B.
FIG. 6C shows the release rate of Compound #1 of the formulations of Table I.
Figure 6A:
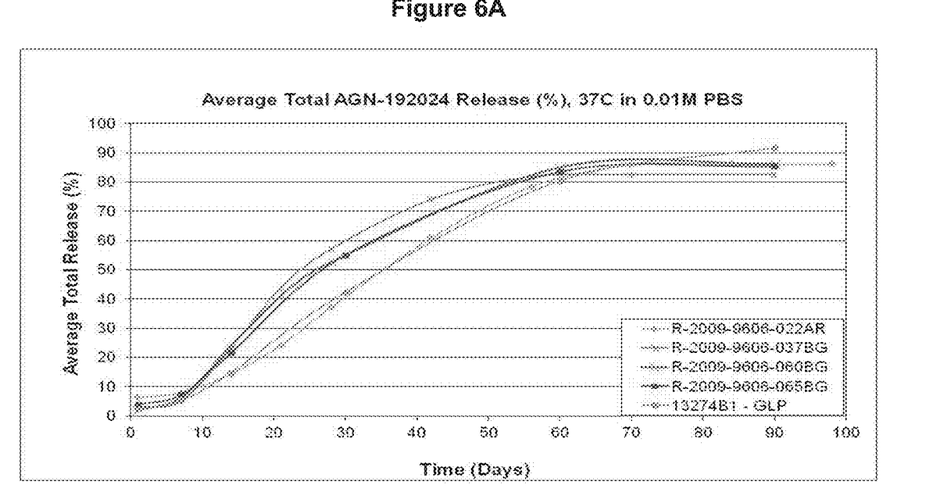
Figure 6B:
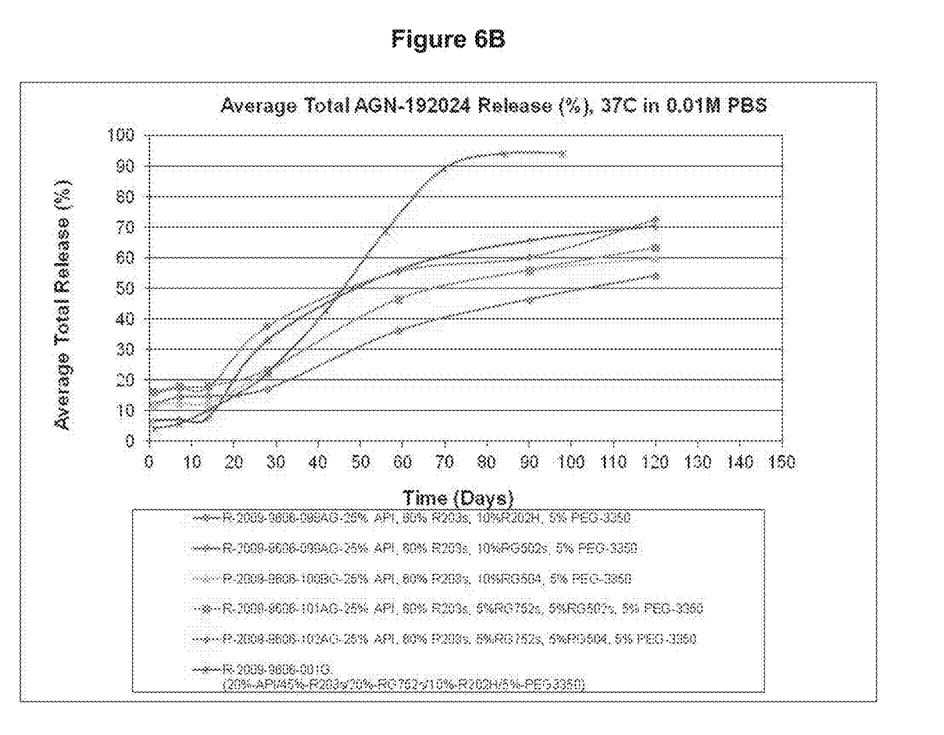

Bimatoprost has been formulated into implants that can be injected or implanted subcutaneously, into visceral fat or in direct apposition to an organ. An example is the following formulation: 20% Bimatoprost, 45% R203s, 20% RG752s 10% R202H, 5% PEG-3350 and FIG. 6A shows the release rate of bimatoprost from this formulation (R203S is an ester end-capped PLA, R202H is an acid end group PLA, RG752S is a 75:25 PLGA with an ester end group and PEG_3350 is polyethylene glycol with a molecular weight of 3350). Other implant formulations and their release rates are shown in FIG. 6B.

Another compound (Compound #1) which may be useful for fat reduction is disclosed below:

Implant formulations with Compound #1 and their properties are in Table I below:

| Examples | Lot # | compositions | implant dimension | implant wt (µg) | in vitro release rate (µg/d) | estimated release duration (month) |
|---|---|---|---|---|---|---|
| 1 | 10524-101 | 8.0% API, 92.0% R202H | 150 µm × 1.5 mm | 36 | 29 | 3 |
| 2 | 10810-061 | 8.0% API, 92.0% R203H | 200 µm × 1.5 mm | 64 | 26 | 6 |
| 3 | 10810-080 | 8.0% API, 51.7% R203S, 23.0% RG752S, 11.5% R202H, 5.8% hexadecanol | 200 µm × 1.5 mm | 64 | 34 | 4-5 |
| 4 | 10810-116 | 8.0% API, 18.4% R203S, 73.6% R203H | 200 µm × 1.5 mm | 64 | 28 | 6 |

Example V

Microspheres

Figure 7A:
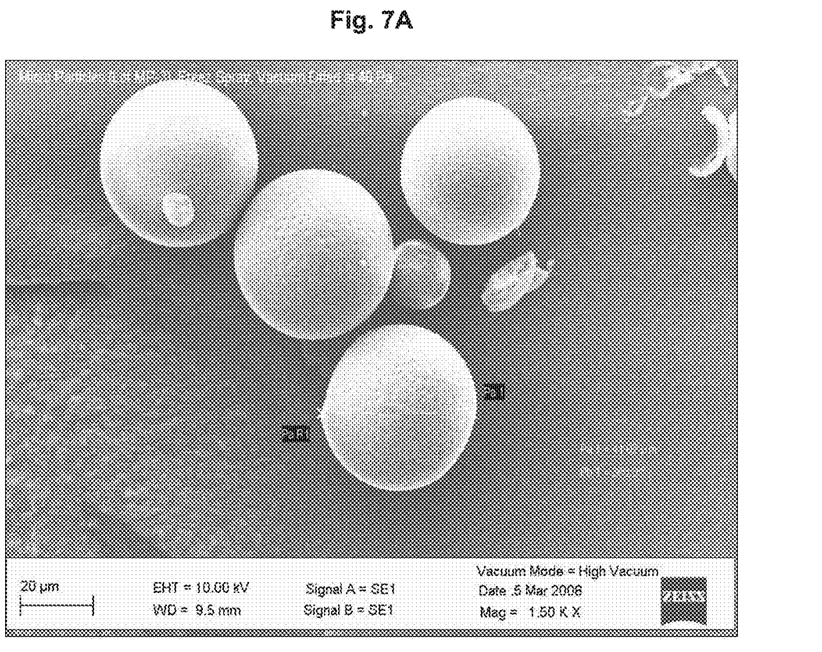
FIG. 7A shows bimatoprost microspheres which can be used for sustained release of bimatoprost for localized fat reduction.
Figure 7B:
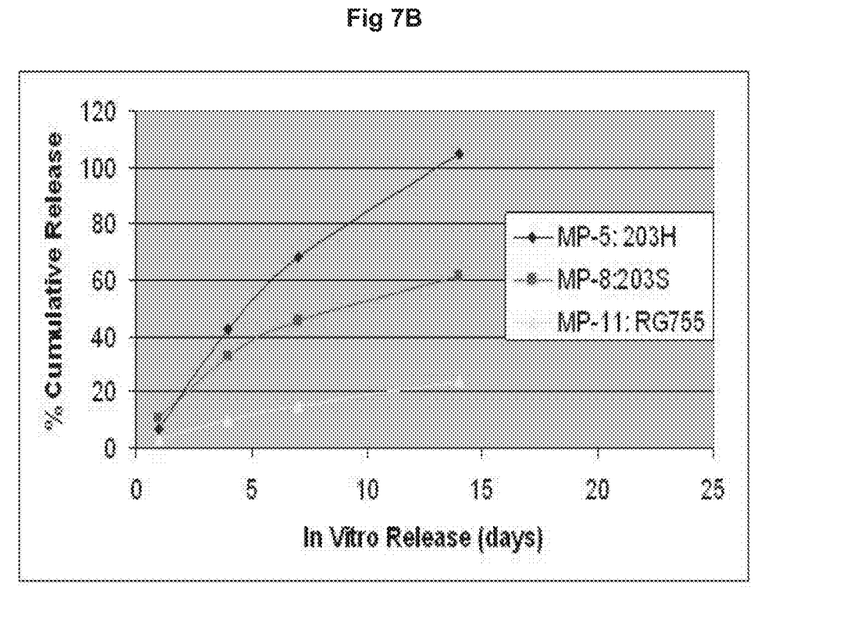
FIG. 7B shows the release rate of bimatoprost from the latanoprost microspheres.

Bimatoprost and latanoprost can also be sustained through the use of PLGA microspheres and macrospheres as shown in FIGS. 7A-7B for latanoprost. Latanoprost microspheres were manufactured from the PLA and PLGA polymers as shown in the table below. The microspheres were manufactured by dissolving 20 mg of latanoprost and 100 mg polymer in 0.8 ml ethyl acetate. A minimum amount of dichloromethane may be added to complete dissolution of the polymer. This solution is added to 40 mL 1% polyvinyl alcohol aqueous solution via a micro-pipette while mixing at high sheer, 3000 rpm, for 5 minutes with a homogenizer.

After shearing, a milky white emulsion is formed, and it is mildly agitated in a fume hood for 3-5 hours to allow solvent evaporation. This dispersion is then centrifuged at 2000 rpm for 15 min to remove supernatant, and then 10 mL water is added to reconstitute the microspheres. The final reconstituted micropsheres are lyophilized. The release of latanoprost from the microspheres into isotonic phosphate buffered saline is shown in FIG. 7B

| Lot number | Polymer | drug load % | entrap efficiency % | PS before freeze drying, um | | |
|---|---|---|---|---|---|---|
| | | | | d10 | d90 | Mean |
| MP-5 | 203H | 13.5% | 81.0% | 15.4 | 59.2 | 31.9 |
| MP-8 | R203S | 12.2% | 73.3% | 15.8 | 64.5 | 34.7 |
| MP-11 | RG755 | 11.9% | 71.3% | 17.4 | 66.3 | 35.6 |

Example VI

Injectable Solvents

Figure 8:
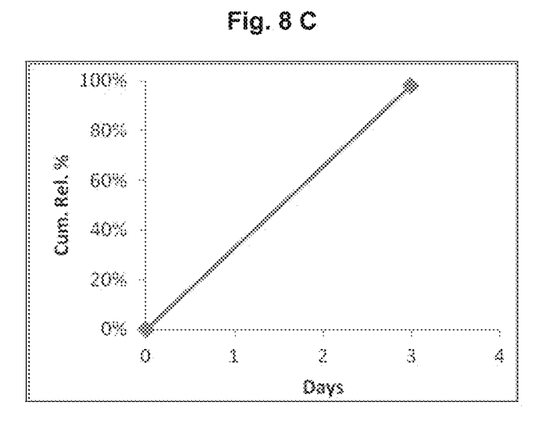
Figure 8A:
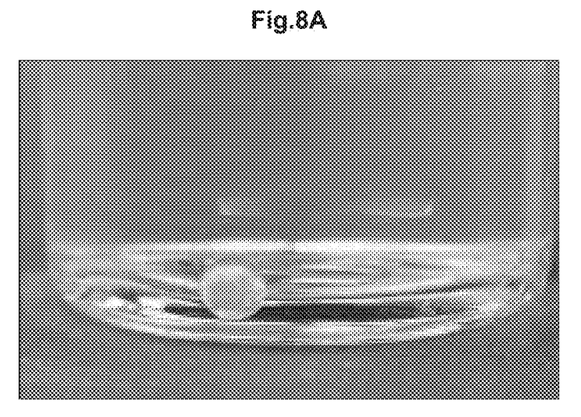
FIGS. 8A and 8B show shows 10% bimatoprost in diethyl glycol dibenzoate (gel); and, FIG. 8C shows an example of bimatoprost release from a 10% Bimatoprost in Diethyl Glycol Dibenzoate depot (gel).
Figure 8B:
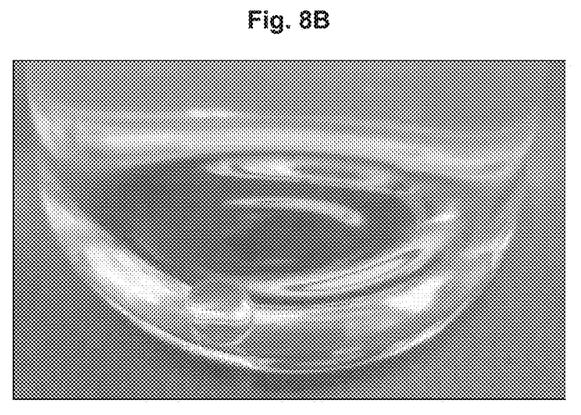

Other excipients such as sucrose acetate isobutyrate, ethyl benzoate. tripropionin, benzyl benzoate. tripropionin, diethyl Gglycol dibenzoate among others can be used for direct injection subcutaneously or into the fat. FIGS. 8A-8B shows 10% bimatoprost in Diethyl Glycol Dibenzoate (gel) and FIG. 8C shows an example of bimatoprost release from 10% Bimatoprost in Diethyl Glycol Dibenzoate (gel).

The invention claimed is:

1. A method of fat reduction comprising injecting a sustained release formulation of Compound #1:

into a fat deposit, wherein the sustained release formulation is an implant with the formulation of about 8% Compound #1 and about 92% R202H poly(D,L-lactide).

2. The method of claim 1, wherein the implant releases compound #1 in the fat deposit for over a period of 100 days.

3. A method of fat reduction comprising injecting a sustained release formulation of Compound #1:

into a fat deposit, wherein the sustained release formulation is an implant with the formulation of about 8% Compound #1 and about 92% R203H poly(D,L-lactide).

4. A method of fat reduction comprising injecting a sustained release formulation of Compound #1:

into a fat deposit, wherein the sustained release formulation is an implant with the formulation of about 8% Compound #1, about 52% R203S poly(D,L-lactide), about 23% RG752S poly(D,L-lactide-co-glycolide), about 11% R202H poly(D,L-lactide), and about 6% hexadecanol.

5. A method of fat reduction comprising injecting a sustained release formulation of Compound #1:

into a fat deposit, wherein the sustained release formulation is an implant with the formulation of about 8% Compound #1, about 18% R203S poly(D,L-lactide), and about 74% R203H poly(D,L-lactide).

6. The method of claim 1, wherein the fat deposit into which the formulation is injected is selected from the group consisting of abdominal fat deposits, visceral fat deposits, epicardial fat deposits, subcutaneous fat deposits, and ectopic fat deposits.

7. The method of claim 3, wherein the fat deposit into which the formulation is injected is selected from the group consisting of abdominal fat deposits, visceral fat deposits, epicardial fat deposits, subcutaneous fat deposits, and ectopic fat deposits.

8. The method of claim 4, wherein the fat deposit into which the formulation is injected is selected from the group consisting of abdominal fat deposits, visceral fat deposits, epicardial fat deposits, subcutaneous fat deposits, and ectopic fat deposits.

9. The method of claim 5, wherein the fat deposit into which the formulation is injected is selected from the group consisting of abdominal fat deposits, visceral fat deposits, epicardial fat deposits, subcutaneous fat deposits, and ectopic fat deposits.

* * * * *